(12) United States Patent
Boeger et al.

(10) Patent No.: US 8,993,813 B2
(45) Date of Patent: Mar. 31, 2015

(54) METHOD FOR PRODUCING PARATHYMOL

(75) Inventors: Uwe Boeger, Leverkusen (DE); Lutz Heuer, Dormagen (DE); Michael Herzhoff, Much (DE)

(73) Assignee: LANXESS Deutschland GmbH, Cologne, DE (US)

( * ) Notice: Subject to any disclaimer, the term of this patent is extended or adjusted under 35 U.S.C. 154(b) by 0 days.

(21) Appl. No.: 14/117,762

(22) PCT Filed: May 18, 2012

(86) PCT No.: PCT/EP2012/059268
§ 371 (c)(1),
(2), (4) Date: Feb. 17, 2014

(87) PCT Pub. No.: WO2012/159991
PCT Pub. Date: Nov. 29, 2012

(65) Prior Publication Data
US 2014/0163261 A1 Jun. 12, 2014

(30) Foreign Application Priority Data

May 20, 2011 (EP) .................................... 11166843

(51) Int. Cl.
C07C 37/72 (2006.01)
C07C 37/14 (2006.01)
C07C 37/84 (2006.01)

(52) U.S. Cl.
CPC ..................................... *C07C 37/84* (2013.01)
USPC ........................... 568/751; 568/756; 568/790

(58) Field of Classification Search
None
See application file for complete search history.

(56) References Cited

U.S. PATENT DOCUMENTS 3,928,471 A * 12/1975 Suda et al. ..................... 568/750
2010/0331579 A1 * 12/2010 Heuer ........................... 568/756

* cited by examiner

Primary Examiner — Brian J Davis
(74) Attorney, Agent, or Firm — Jennifer R. Seng

(57) ABSTRACT

The present invention relates to a process for the preparation of 4-isopropyl-3-methylphenol (p-thymol) from distillation residues of thymol production.

15 Claims, No Drawings

METHOD FOR PRODUCING PARATHYMOL

The present invention relates to a process for the preparation of 4-isopropyl-3-methylphenol (p-thymol) from distillation residues of thymol production.

4-Isopropyl-3-methylphenol is used for example as an antibacterial and microbicidal agent in cosmetics and mouthwashes with antiplaque action and also foot care and hair care compositions with good skin compatibility. The preparation of 4-isopropyl-3-methylphenol is known in principle.

Thus, U.S. Pat. No. 3,331,879 describes the reaction of meta-cresol (m-cresol, 3-methylphenol) with propene over a zirconium catalyst, where essentially thymol (2-isopropyl-5-methylphenol), but also many aromatic by-products are formed. As one by-product, 4-isopropyl-3-methylphenol was identified with a content of 2% in the reaction mixture and 4.4% after a first distillation. Isolation of the 4-isopropyl-3-methylphenol is not described.

DE 2139622 OS describes the production of up to 19.5% of 4-isopropyl-3-methylphenol during the reaction of m-cresol with propene over an acidic zinc catalyst. Isolation of the 4-isopropyl-3-methylphenol is not described here either.

DE 2528303 OS describes the production of ca. 2% of 4-isopropyl-3-methylphenol during the reaction of meta-cresol with propene over a basic aluminum oxide catalyst. Isolation of the 4-isopropyl-3-methylphenol from the various by-products is not described.

Furthermore, it is known from U.S. Pat. No. 2,603,662 to obtain 4-isopropyl-3-methylphenol by means of a complex process as a by-product in the reaction of meta-cresol with isobutene.

A common aspect of all of the aforementioned processes is that 4-isopropyl-3-methylphenol is produced as secondary component during the alkylation of m-cresol with so many other secondary components that isolation was either not carried out or takes place by means of extraordinarily laborious methods.

DE 102007035515 A discloses a process in which thymol and unreacted meta-cresol are largely separated off firstly by distillation from a reaction mixture from the thymol production, and the residue remaining as a result is distilled in order to separate off nonvolatile or very substantially nonvolatile substances, and the distillate obtained in this way is crystallized after adding up to 5% by weight of water, or the remaining residue is crystallized after adding up to 5% by weight of water, and the crystallized residue is separated from nonvolatile or very substantially nonvolatile substances by distillation.

The resulting purity of the 4-isopropyl-3-methylphenol was 95.1%.

There was therefore the need to provide a process with which 4-isopropyl-3-methylphenol can be obtained in an efficient manner and in high purity.

A process has now been found for the preparation of 4-isopropyl-3-methylphenol from reaction mixtures which are obtained during the reaction of meta-cresol with propene in the presence of a catalyst, which process is characterized in that a) thymol and unreacted meta-cresol are largely removed by distillation from the reaction mixture, giving a distillation residue, and
b) crude 4-isopropyl-3-methylphenol is obtained by crystallization from the distillation residue remaining according to step a) and
c) the crude 4-isopropyl-3-methylphenol obtained according to step b) is treated with an organic solvent which consists to at least 80% by weight of hydrocarbons or halogenated hydrocarbons or a mixture thereof.

The scope of the invention encompasses only not the specified ranges and preferred ranges of formulae and parameters, but also any desired combinations thereof even if they have not been explicitly listed in their entirety below for practical reasons.

The alkylation of meta-cresol with propene in the presence of a catalyst, which can be carried out in a manner known to the person skilled in the art (see e.g. DE 3824284 OS or DE 2528303 OS), typically produces a reaction mixture which, besides a main amount of thymol, also comprises about 1 to 3% by weight of 4-isopropyl-3-methylphenol.

In a step a) of the process according to the invention, thymol and unreacted meta-cresol are largely removed by distillation from the reaction mixture. The term "largely" means here that the remaining residue has a fraction of thymol and meta-cresol of, when taken together, in total 80% or less, preferably 55% or less and particularly preferably 30% or less.

The distillation can be carried out here in a manner known per se for example discontinuously or continuously, preference being given to a continuous distillation under a pressure that is reduced compared to atmospheric pressure and which can be for example 1 to 950 hPa, preferably from 50 to 950 and particularly preferably from 50 to 150 hPa.

The temperature during the distillation at the top of the column is for example from 100 to 225° C. and preferably from 140 to 155° C., and the bottom temperature is for example from 120 to 260° C. and preferably from 170 to 190° C., it being clear to the person skilled in the art that the temperatures during the distillation at the top of the column and in the bottom correlate with one another and also with the distillation pressure. Suitable distillation conditions are easy to ascertain for the person skilled in the art.

Preferably, the distillation takes place with the help of a short-path evaporator, a column without internals or by means of a falling-film evaporator or else a thin-film evaporator. One theoretical plate is adequate for the distillation. The use of more than one plate is naturally possible but unnecessary.

Typically, the remaining residue comprises, besides 4-isopropyl-3-methylphenol, 20 to 30 further secondary components of low molecular structure and also polymeric secondary components. After the distillation, the content of 4-isopropyl-3-methylphenol in the remaining residue, which is usually black in color, is typically 10 to 30% by weight.

According to step b), crude 4-isopropyl-3-methylphenol is crystallized out from the residue remaining according to step a). Preferably, this is accomplished by cooling the residue remaining according to step a), in which case the temperature difference during cooling can be for example 30 K or more, preferably 40 K or more, more preferably 40 to 100 K.

Since the residue from the distillation that remains according to step a) following removal from the distillation apparatus typically has a temperature of 140 to 180° C. and preferably from 120 to 140° C., the crystallization is accomplished particularly readily by simply cooling the residue, for example to temperatures of 30° C. or less, preferably to 25° C. or less, particularly preferably to between −10° and 25° C.

During the cooling, stirring may or may not be performed, but is preferred.

In one embodiment of the process according to the invention, the crystallization can be induced or accelerated by seeding with crystalline 4-isopropyl-3-methylphenol.

The duration of the crystallization is typically 0.5 to 200 hours, preferably 1 to 48 hours and particularly preferably 2 to 24 hours.

According to step b), crude 4-isopropyl-3-methylphenol is obtained by crystallization. The degree of purity of the crude 4-isopropyl-3-methylphenol obtained in this way is about 75 to 90% by weight, preferably 80 to 90% by weight.

Separating off the crude 4-isopropyl-3-methylphenol from the mother liquor can take place in a manner known per se by sedimentation and decantation, filtration or centrifugation or other solid-liquid separating operations known to the person skilled in the art.

The fraction of 4-isopropyl-3-methylphenol is about 60 to 90% by weight, preferably 70 to 90% by weight, based on the content of 4-isopropyl-3-methylphenol in the distillation residue used for step b).

The crude 4-isopropyl-3-methylphenol obtained according to step b) is treated in step c) with an organic solvent which consists to at least 80% by weight of hydrocarbons or halogenated hydrocarbons or a mixture thereof. In the context of the invention, the term "treatment" is understood as meaning both "washing with" and also "recrystallization from" as well as any desired combinations of these processes.

The organic solvent used for the treatment consists to at least 80% by weight, preferably to at least 90% by weight and particularly preferably to at least 98% by weight, of hydrocarbons or halogenated hydrocarbons or a mixture thereof, where particularly preferred solvents used are exclusively hydrocarbons or halogenated hydrocarbons as are commercially available in technical or laboratory grade.

Hydrocarbons or halogenated hydrocarbons are preferably those which have a boiling point of 30 to 160° C. at 1013 hPa.

Preferred hydrocarbons are cyclopentane, cyclohexane, n-hexane, 2-methylpentane, 3-methylpentane, methylcyclopentane, 2,2-dimethylbutane, 2,3-dimethylbutane, methylcyclohexane, 2,2-dimethylpentane, 2,3-dimethylpentane, 2,4-dimethylpentane, n-heptane, n-octane, isooctane or mixtures thereof, with methylcyclohexane being particularly preferred.

Preferred halogenated hydrocarbons are dichloromethane, chlorobenzene, the isomeric dichlorobenzenes or mixtures of the aforementioned solvents, with dichloromethane and chlorobenzene being preferred.

If washing is carried out, the washing can take place for example with 0.5 to 100 weight equivalents of the solvent based on the crude 4-isopropyl-3-methylphenol, preferably with 0.5 to 10 weight equivalents.

If washing is carried out, the washing can take place for example at −10° C. up to the boiling point of the solvent used.

If recrystallization is carried out, the recrystallization can take place for example with 0.5 to 20 weight equivalents of the solvent based on the crude 4-isopropyl-3-methylphenol, preferably with 0.5 to 10 weight equivalents, in which case the solubility behavior as a function of the temperature can be taken into consideration and preferably is taken into consideration.

It is easily possible for the person skilled in the art to identify suitable conditions both for the washing and also for the recrystallization in a few preliminary experiments.

In one embodiment, the recrystallization takes place with the addition of filter aids or activated carbon, in which case then the filter aid or aids or the activated carbon is removed again by filtration before crystallization of the 4-isopropyl-3-methylphenol from the solvent.

Step c) can optionally be repeated. If step c) includes a recrystallization, the repetition of step c) is not preferred.

The particular advantage of the invention is considered to be the fact that 4-isopropyl-3-methylphenol can be recovered efficiently and in extraordinarily high purity as secondary component in the production of thymol despite the presence of very many further secondary components that are likewise solid at room temperature. The purity, if washing is carried out in step c), is typically 98 to 99% by weight, upon recrystallization typically 98.5 to 99.99% by weight, preferably 99.8 to 99.99% by weight.

Example 1

21.1 kg of a 60° C.-warm, black distillation residue from the production of thymol by reaction of m-cresol with propene in the presence of a catalyst, the distillation residue comprising 21.5% by weight of thymol, 7.0% by weight of 3-isopropyl-5-methylphenol, 25.0% by weight of 4-isopropyl-3-methylphenol, 21.5% by weight of 2,6-diisopropyl-3-methylphenol, 21.0% by weight of 2,4-diisopropyl-5-methylphenol and about 22 different, in total ca. 4% by weight of other alkylated cresols, were cooled slowly to room temperature, with stirring, in a 25 l capacity reactor over the course of 16 hours, during which the 4-isopropyl-3-methylphenol crystallized out. The precipitated, crude 4-isopropyl-3-methylphenol was filtered off. 5.26 kg of 4-isopropyl-3-methylphenol with a purity of 83.4% by weight were obtained, which corresponded to a yield of 82.3% by weight of the 4-isopropyl-3-methylphenol present in the distillation residue.

Example 2

In each case 50 g of the crude 4-isopropyl-3-methylphenol according to example 1 were washed with 150 g of an organic solvent at 20° C. with stirring on a suction filter. The results are shown in table 1.

TABLE 1

| Example | Solvent | Yield [% by weight] | Purity [% by weight] |
|---|---|---|---|
| 2a | Cyclohexane | 90 | 98.53 |
| 2b | n-Hexane | 94 | 98.08 |
| 2c | Dichloromethane | 63 | 98.76 |
| 2d | Chlorobenzene | 90 | 98.87 |
| 2e | Methylcyclohexane | 92 | 98.85 |
| 2f (for comparison) | Ethyl acetate | 0 | — |
| 2g (for comparison) | tert-Butyl methyl ether | 0 | — |
| 2h (for comparison) | Isopropanol | 0 | — |
| 2i (duplicate washing) | Methylcyclohexane | 86 | 99.37 |

Example 2k

In each case 50 g of the crude 4-isopropyl-3-methylphenol according to example 1 were heated to 85° C., with stirring, with 188 g of methylcyclohexane and 0.5 g of activated carbon and stirred at this temperature for 15 min and the activated carbon was filtered off. The filtrate was then left to cool to room temperature with stirring. The p-thymol that crystallized out during the reaction was filtered off and dried. This gave in total 75% by weight of the p-thymol used as snow-white needles with a purity of 99.90% by weight.

What is claimed is:

1. A process for the preparation of 4-isopropyl-3-methylphenol from reaction mixtures which are obtained during the reaction of meta-cresol with propene in the presence of a catalyst, characterized in that a) thymol and unreacted meta-cresol are removed by distillation from the reaction mixture, giving a distillation residue that has a fraction of thymol and metacresol, when taken together in total 80%,
b) crude 4-isopropyl-3-methylphenol is obtained by crystallization from the distillation residue remaining from step a), and
c) the crude 4-isopropyl-3-methylphenol obtained according to step b) is treated with an organic solvent which consists of at least 80% by weight of hydrocarbons or halogenated hydrocarbons or a mixture thereof.

2. The process as claimed in claim 1, characterized in that the residue according to step a) comprises 10 to 30% by weight of 4-isopropyl-3-methylphenol.

3. The process as claimed in claim 1 characterized in that, in step b), the crystallization takes places by cooling the residue which remains according to step a), the temperature difference during cooling being 30 K or more.

4. The process as claimed in claim 1, characterized in that stirring is carried out during cooling in step b).

5. The process as claimed in claim 1, characterized in that in step b) the crystallization is induced or accelerated by seeding with crystalline 4-isopropyl-3-methylphenol.

6. The process as claimed in claim 1, characterized in that the degree of purity of the crude 4-isopropyl-3-methylphenol obtained in step b) is 75 to 90% by weight.

7. The process as claimed in claim 1, characterized in that the fraction of the crude 4-isopropyl-3-methylphenol obtained in step b) is 60 to 90% by weight, based on the content of 4-Isopropyl-3-methylphenol in the distillation residue used for step b).

8. The process as claimed in claim 1, characterized in that the organic solvent used in step c) consists of at least 90% by weight, of hydrocarbons or halogenated hydrocarbons or a mixture thereof.

9. The process as claimed in claim 1 characterized in that the hydrocarbons or halogenated hydrocarbons are those which have a boiling point of 30 to 160° C. at 1013 hPa.

10. The process as claimed in claim 1, characterized in that the hydrocarbons are selected from the group consisting of cyclopentane, cyclohexane, n-hexane, 2-methylpentane, 3-methylpentane, methylcyclopentane, 2,2-dimethylbutane, 2,3-dimethylbutane, methylcyclohexane, 2,2-dimethylpentane, 2,3-dimethylpentane, 2,4-dimethylpentane, n-heptane, n-octane, isooctane or mixtures thereof.

11. The process as claimed in claim 1, characterized in that the halogenated hydrocarbons are selected from the group consisting of dichloromethane, chlorobenzene, the isomeric dichlorobenzenes or mixtures of the aforementioned solvents.

12. The process as claimed in claim 1, wherein step c includes washing with 0.5 to 100 equivalents by weight of the solvent, based on the crude 4-isopropyl-3-methylphenol.

13. The process as claimed in claim 1, wherein step c includes recrystallization with 0.5 to 20 equivalents by weight of the solvent based on the crude 4-isopropyl-3-methylphenol.

14. The process as claimed in claim 1, characterized in that step c) takes place by recrystallization and the recrystallization takes place by adding filter aids or activated carbon.

15. The process as claimed in claim 1, characterized in that step c) is repeated.

\* \* \* \* \*